US011568996B2

(12) United States Patent
Li et al.

(10) Patent No.: US 11,568,996 B2
(45) Date of Patent: Jan. 31, 2023

(54) CROSS-DEPARTMENTAL CHRONIC KIDNEY DISEASE EARLY DIAGNOSIS AND DECISION SUPPORT SYSTEM BASED ON KNOWLEDGE GRAPH

(71) Applicant: ZHEJIANG LAB, Hangzhou (CN)

(72) Inventors: Jingsong Li, Hangzhou (CN); Yu Tian, Hangzhou (CN); Yong Shang, Hangzhou (CN); Ran Xin, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 17/541,301

(22) Filed: Dec. 3, 2021

(65) Prior Publication Data

US 2022/0093268 A1    Mar. 24, 2022

Related U.S. Application Data

(63) Continuation of application No. PCT/CN2021/071825, filed on Jan. 14, 2021.

(30) Foreign Application Priority Data

Jan. 14, 2020  (CN) .......................... 202010039000.8

(51) Int. Cl.
*G16H 10/60* (2018.01)
*G16H 50/50* (2018.01)
*G16H 50/20* (2018.01)

(52) U.S. Cl.
CPC ............. *G16H 50/50* (2018.01); *G16H 10/60* (2018.01); *G16H 50/20* (2018.01)

(58) Field of Classification Search
CPC ......... G16H 50/50; G16H 10/60; G16H 50/20
See application file for complete search history.

(56) References Cited

U.S. PATENT DOCUMENTS

2013/0096947 A1    4/2013  Shah et al.
2019/0074082 A1*   3/2019  Buckler ............... G06T 7/0012
(Continued)

FOREIGN PATENT DOCUMENTS

CN    110600121 A    12/2019
CN    111370127 A     7/2020

OTHER PUBLICATIONS

International Search Report (PCT/CN2021/071825); dated Apr. 2, 2021.

(Continued)

*Primary Examiner* — Mohamed Charioui
*Assistant Examiner* — Christine Y Liao
(74) *Attorney, Agent, or Firm* — W&G Law Group

(57) ABSTRACT

Provided is a cross-departmental decision support system for early diagnosis of a chronic kidney disease based on knowledge graph, which comprises a patient information model building module, a patient information model library storage module, a knowledge graph association module, a knowledge graph inference module and a decision support feedback module. According to the present application, by constructing a patient information model and utilizing an OMOP CDM standard terminology system, patient electronic medical record data is constructed into a patient information model with unified concept coding and unified semantic structure; making full use of the advantages of semantic technology in data interactivity and scalability, so that the system has better adaptability and scalability to heterogeneous data in different hospitals.

5 Claims, 4 Drawing Sheets

(56) References Cited

U.S. PATENT DOCUMENTS

2020/0051694 A1* 2/2020 Goldberg ............... G16H 10/60
2020/0286596 A1* 9/2020 Yang ...................... G16H 70/20

OTHER PUBLICATIONS

Analysis of Chronic Kidney Disease Decision Support Model Based on Clinical Knowledge Graph; Date of Mailing: Dec. 20, 2018.

* cited by examiner

CROSS-DEPARTMENTAL CHRONIC KIDNEY DISEASE EARLY DIAGNOSIS AND DECISION SUPPORT SYSTEM BASED ON KNOWLEDGE GRAPH

CROSS-REFERENCE TO RELATED APPLICATIONS

The present application is a continuation of International Application No. PCT/CN2021/071825, filed on Jan. 14, 2021, which claims priority to Chinese Application No. 202010039000.8, filed on Jan. 14, 2020, the contents of both of which are incorporated herein by reference in their entireties.

TECHNICAL FIELD

The present application relates to a knowledge graph technology and a decision support technology for early diagnosis of chronic diseases, in particular to a cross-departmental decision support system for early diagnosis of chronic kidney diseases based on knowledge graph.

BACKGROUND

Chronic kidney disease (CKD) is a major chronic disease that seriously endangers human health, and will significantly increase the morbidity and mortality of cardiovascular diseases. Epidemiological survey in China shows that the prevalence rate of the CKD has reached 10.8%, and it is estimated that there are more than 100 million CKD patients in China. However, the survey shows that the awareness and awareness rate of kidney diseases in basic hospitals and non-nephrologists in China is low: the awareness rate of chronic kidney diseases among the general population is only 12.5%, while the treatment rate is as low as 7.5%. International research shows that the basic level physicians of non-nephrology have only 30% knowledge of diagnosis and treatment of chronic kidney diseases. The lack of non-nephrologists for cognition of chronic kidney diseases leads to many patients with chronic kidney disease failing to find their illness in time, which leads to an increase in the risk of end-stage kidney diseases and cardiovascular diseases, and brings a huge medical burden. Therefore, it is necessary to study the cross-departmental clinical decision support method and system for early diagnosis of chronic kidney diseases for non-nephrologists, so as to assist non-nephrologists to discover the risk of chronic kidney diseases in time and improve the awareness rate and treatment rate of chronic kidney diseases.

There are two main technical solutions for early diagnosis and decision support of chronic kidney diseases: one is an expert system based on electronic medical records, which sets certain criteria for judging chronic kidney disease indicators and combines with electronic medical records to diagnose and warn chronic kidney diseases. The other is based on machine learning technology, using support vector machine (SVM), convolutional neural network (RNN) and other algorithms to provide auxiliary support. For example, the risk of a chronic kidney disease is given by modeling and evaluating the clinical examination indicators of the patients; by analyzing the similar cases of the patients, it can provide physicians with similar previous cases of the chronic kidney disease.

The existing decision support technology for early diagnosis of chronic kidney diseases has the following problems: (1) the current expert system based on the electronic medical record is often deeply integrated with the hospital electronic medical record system, and uses specific data structure and medical terminology system, which leads to its poor scalability and portability, and is often not suitable for many different hospitals; at the same time, the established diagnostic rules are difficult to expand and cannot be updated with the changes of clinical guidelines for chronic kidney diseases. (2) based on the auxiliary support of machine learning, it is necessary to input a large number of patient clinical examination and diagnosis data as the training features of the model, and the patient electronic medical record data often lacks sufficient examination results, resulting in poor applicability of the machine learning model; in addition, the machine learning model cannot give a clear diagnosis reason, but can only provide the risk level, resulting in the lack of trust of the clinicians in the system.

SUMMARY

The purpose of the present application is to provide a cross-departmental decision support system for early diagnosis of a chronic kidney disease based on knowledge graph, to help non-nephrologists find patients with missed diagnosis of chronic kidney diseases and high-risk patients in time, and to improve the scalability and adaptability of the system. According to the present application, the medical knowledge graph technology is organically combined with the electronic medical record, the medical knowledge graph for early diagnosis and treatment of chronic kidney disease is constructed, and complex electronic medical record data is converted into a patient-centered graph patient information model, so as to provide decision support for early diagnosis of chronic kidney diseases. The knowledge graph has strong data interaction ability and strong expansion ability, and provides standardized expression of medical concepts; semantic mapping can adapt to the heterogeneous electronic medical record data structure and terminology system in many hospitals, thus realizing the application of the decision support system in many hospitals. The knowledge graph gives decision support conclusions through semantic inference, and its inference path can be traced back to the whole process. It can not only give clinical recommendations, but also provide guidelines and expert experiences corresponding to the semantic inference, and give reasons for clinical recommendations, thus enhancing the physicians' trust in the system.

The purpose of the present application is realized by the following technical solution: a cross-departmental decision support system for early diagnosis of a chronic kidney disease based on knowledge graph, including a patient information model building module, a patient information model library storage module, a knowledge graph association module, a knowledge graph inference module and a decision support feedback module; wherein the patient information model building module is used for building a patient-centered patient electronic medical record data knowledge sub-graph based on patient electronic medical record data and according to a semantic structure of a chronic kidney disease knowledge graph and an OMOP CDM data structure to form a patient information model;

the patient information model library storage module provides support for storage and calling of the patient information mode, stores the patient information model in a RDF triple form by establishing a knowledge graph database, and provides a query and modification interface of the patient information model by a SPARQL endpoint; construct a SPARQL query statement template according to content and structure of patient data needed for early diagnosis of the chronic kidney disease, and provides a general method for retrieving the patient information model so as to support the knowledge graph inference of the decision support;

the knowledge graph association module enriches semantic information of the patient information model, and associates scattered clinical record RDF triples in the patient information model according to a real world clinical diagnosis and treatment process sequence; associates individuals of medical examinations, clinical complaints and prescription records with clinical findings, clinical diagnoses and disease risks based on a medical concept relationship in the chronic kidney disease knowledge graph;

the knowledge graph inference module reasons diagnosis deficiency, disease risk diagnosis deficiency, disease follow-up requirement deficiency and prescription adjustment for the chronic kidney disease of a patient based on the RDF triple relationship of clinical records in the patient information model and clinical recommendation inference rules in the chronic kidney disease knowledge graph, and provides corresponding clinical diagnosis recommendations, risk recommendations, follow-up requirement recommendations and prescription adjustment recommendations based on inference results; and the decision support feedback module feeds back the clinical diagnosis recommendations, risk recommendations, follow-up requirement recommendations and prescription adjustment recommendations provided by the knowledge graph inference module, and a clinical recommendation report containing inference process of above recommendations to a physician.

Furthermore, in the patient information model building module, model building comprises two processes which are patient data analysis and patient data RDF semantic transformation:

(1) patient data analysis process: according to the electronic medical record data of the patient, the patient data is divided into multiple hierarchical structures according to the chronic kidney disease knowledge graph and the standard terminology coding and structure of OMOP CDM; for each patient P, there are multiple medical records $V_i(i=1 \ldots n)$, where $\{V_i|i=1 \ldots n\} \subset P$; wherein $V_i \cap V_j = \emptyset$, $(V_i, V_j) \subset P$; each visit record $V_i$ spans a time period T, and for information such as any piece of diagnosis record D, examination record M, prescription record Pr and operation record Pc in the patient data, $\{D_h, M_j, Pr_k, Pc_m | h, j, k, m=1 \ldots n\} \subset V_i$ when a record time thereof is within the time period T; the concept coding, relationship type, value type and value information are extracted from subitems of D, M, Pr and Pc;

(2) a RDF semantic transformation process of the patient data: based on the analysis results of the patient data and the semantic structure of the chronic kidney disease knowledge graph, the patient electronic medical record data is constructed into RDF triple relationships conforming to OWL language specification, and a data field is converted to standard OMOP CDM terminology coding through semantic mapping; for each patient P, visit record V, examination record M and prescription record Pr in the patient data, an ontology individual is constructed with a data ID thereof as a URI to form a corresponding individual diagram; for each patient individual $P_{ind}$, visit record individual $V_{ind}$, examination record individual $M_{ind}$ and prescription record individual $Pr_{ind}$, a corresponding ontology class relationship is constructed to form a corresponding class diagram; based on a hierarchical relationship intercepted in patient data analysis, association between the patient individual $P_{ind}$ and the visit record individual association between the visit record individual $V_{ind}$ and the examination record individual $M_{ind}$, and association between the visit record individual $V_{ind}$ and the prescription record individual $Pr_{ind}$ are established through ontology object properties to form a patient data relationship diagram and a visit record relationship diagram; for each diagnostic record D and operation record Pc, a relationship between the related medical record individual $V_{ind}$ and a disease ontology class and an operation record ontology class is established to form a corresponding class diagram; the patient data is constructed into RDF triple data according to the above rules, and the patient information model is formed.

Furthermore, the patient information model library storage module is divided into three parts: a Jena TDB storage terminal, a Jena Fuseki SPARQL endpoint and a control terminal;

the Jena TDB storage terminal is configured to build a knowledge graph database to store the patient information model in a form of RDF triples, wherein all patient information models converted into the RDF triples are recorded as N-Triple data files conforming to OWL language rules in a form of <s,p,o>; a RDF triple data set is stored and transformed by a Jena TDB Loader, and indices of a head element S, a relation element P and a tail element O of the RDF triple is established to improve the query speed;

the Jena Fuseki SPARQL endpoint is configured to build a RDF triple query and modification interface; the Jena Fuseki SPARQL endpoint invokes Jena TDB storage content, and invokes and modifies the patient information model through a W3C standard SPARQL query statement; the Jena Fuseki SPARQL endpoint is built in a Tomcat server, which monitors a SPARQL query request through a HTTP request and feeds back corresponding results;

the control terminal provides a target query and modification function for the patient information model; according to patient information model structure and knowledge graph inference requirements, a SPARQL query statement template is preset, and a request is sent to the Jena Fuseki SPARQL endpoint and the output result is formatted; for each patient $P_{ind}$, according to the clinical records in the patient information model, a result of a patient data relationship diagram is queried; based on the visit record individual $V_{ind}$ that has been fed back, a result of the medical record relationship diagram is queried; finally, the data property information is queried according to the examination record individual $M_{ind}$ and the operation record individual $P_{rind}$; the control terminal sets SPARQL query statements based on the above principles, and establishes a result graph for feedback.

Furthermore, the knowledge graph association module is implemented as follows:

the chronic kidney disease knowledge graph is defined as $G=(V,A)$, and the patient information model is defined as $G'=(V',A')$, where G and G' are two directed graphs, V and V' are nodes in the graph, and A and A' are directed edges in the graph; the knowledge graph association module completes V' and A' of the graph G' based on the relationship in the graph G; for any $v \in V$ and any $v' \in V'$, node similarities $sim(v,v')$ and $sim'(v',v)$ are calculated, and the similarity through cos similarity; at the same time, similarity matching is carried out according to a standard concept coding hierarchy relationship between nodes v and v'; a similar node pair is recorded as $b=min|sim(v_i,v_j')-sim'(v_j',v_i)|$, a set thereof is $b \in B$, and the node pairs $v_i$ and $v_j$ contained in B are candidate associated node pairs; for the candidate association node pairs, the semantic association similarity of the nodes is calculated, and the triple relationship is supplemented to the patient information model according to the similar association, so as to improve the information; a triple $(v_i,a,v_j) \in V \times A \times V$ is established for the node v and directed edge A, where $(v_i,a,v_j)$ conforms to the graph relationship of G=(V,A); the calculation of semantic association is recorded as rel(v,a)={x|v,x∈V∧∧(v,a,x)∈A}; for each patient information model node $v_i'$, $sim(v,v_i)$ of the corresponding knowledge graph node v is calculated, where $(v,v_i) \in V$ and $v_i \neq v$; all node pairs v and vi whose sim(v,vi) is greater than the threshold k are taken, and if v and vi conform to rel(v,a) relationship, a $<v_{i40},a,v_i>$ triple association to the node $v_1'$ of the patient information model is added, thereby realizing semantic information completion of the patient information model based on the chronic kidney disease knowledge graph.

Furthermore, the knowledge graph inference module is implemented as follows:

firstly, the patient information model is invoked to analyze the RDF triple relationship therein; at the same time, an inference ontology copy $O_n$ is established from the chronic kidney disease knowledge graph, and according to each individual S and an ontology class C to which the individual S belongs in the patient information model, the individual is constructed into an ontology class C' corresponding to the inference ontology copy $O_n$; each individual S and a relation graph R thereof in the patient information model are extracted to obtain a$<s_i,r,s_j>$triple, where $(s_i,s_j) \in S, r \in R$, which is reconstructed in the inference ontology copy on; each individual S and a data property relationship $R_S$ and an attribute Value $V_a$ thereof in the patient information model are extracted to obtain a$<s,r_S,v_a>$triple, where $s \in S, r_s \in R_S$, $v_a \in V_a$, which is reconstructed in the inference ontology copy $O_n$, in the above steps, the inference ontology copy on of chronic kidney disease knowledge graph containing patient information is constructed to provide basic elements for semantic inference;

then, based on OWL2 DL rules in the chronic kidney disease knowledge graph, by using the Fact++inference engine, according to the patient information in the inference ontology copy $O_n$, the patient individual $S_P$, the visit record individual SV, the examination record individual $S_M$ and the prescription record individual $S_{Pr}$ are subjected to ontology class affiliation completion and missing object property establishment; according to OWL2 DL rules in the chronic kidney disease knowledge graph, the data in the patient information model, such as examination record individuals of abnormal glomerular filtration rate, prescription record individuals containing drugs that may damage renal function, and visit record individuals containing chief complaints of chronic kidney disease symptoms, are associated with the chronic kidney disease risk ontology class; object property association is established for the visit record individual $S_{V'}$, including abnormal examination record individual $S_{M'}$ and prescription record individual $S_{pr'}$, and abnormal records in the visit records are marked;

according to Jean Rules established in the clinical guidelines for chronic kidney diseases, by using Jena inference engine, the association between a patient individual $S_P$ and a visit record individual $S_V$ and a clinical recommendation individual $S_{re}$ such as disease diagnosis, risk factors, follow-up plans and drug adjustment plans in the chronic kidney disease knowledge graph is established through semantic inference based on the individual data and the individual relationship in the patient information model, thus forming clinical recommendation contents based on the patient's condition; the Jean Rules established in the clinical guidelines for chronic kidney diseases are divided into diagnosis rules, risk classification rules, follow-up screening rules and prescription adjustment rules for chronic kidney diseases; the above rules are based on a Jena Rules standard language, and are established according to the paradigm of [rule name: (triple 1) (triple 2) . . . operator 1 (operand) operator 2 (operand) . . . →(triple N) (triple N+1) . . .]; according to the specifications of diagnosis, risk grading, follow-up screening and prescription adjustment for chronic kidney diseases the in clinical guidelines, RDF triples containing medical examination results, chief complaint symptoms, disease history, prescription and other information of the patient are established on the left side of the arrow as conditions, a numerical value of that examination result is judged by operators and operands, and RDF triples of disease diagnosis, risk classification, follow-up screening and prescription adjustment are established on the right side of the arrow when the conditions on the left side of the arrow are met; the Jena inference engine implements inference according to the RDF triple information corresponding to the patient individual $S_P$ in the patient information model based on the requirements on the left side of the arrow, and adds a decision support recommendation RDF triple on the right side of the arrow to the patient individual $S_P$ that meets the rules;

according to the inference rules triggered by a Fact++ inference engine and a Jena inference engine, the inference individual $S_R$ is established, and the inference individual $S_R$ is configured to record the clinical knowledge in the clinical guidelines involved in inference; attributes of a relation between the inference individual $S_R$ and the visit record individual $S_v$, the examination record individual $S_M$ and the prescription record $S_{Pr}$ involved in the inference rules are established, so as to establish inference result association for the clinical recommendations and provide a recommendation reason inference process record.

Furthermore, the decision support feedback module is specifically implemented as follows:

the class, object property and data property content of the patient individual $S_P$ in a regular inference ontology $O_n$ are queried through a preset SPARQL query statement, the obtained RDF graph results are analyzed, and the relevant information (concept coding, concept name, numerical value, text information, etc.) of tail nodes in the RDF triple are extracted, so as to obtain the newly established individual $S_{re}$ of diagnosis, risk, follow-up recommendations and prescription adjustment recommendations for the chronic kidney disease; the diagnosis, the risk, the follow-up recommendations and the prescription adjustment recommendations for the chronic kidney diseases that are newly established by the inference module are obtained from $S_{re}$, and a clinical recommendation report containing inference process is formed by combining an inference path relationship recorded in the inference individual $S_R$ corresponding to the patient individual $S_P$ and the recommendation individual $S_{RE}$ for feedback to physicians.

The method has the beneficial effects that the patient electronic medical record data is constructed into the patient information model with unified concept coding and semantic structure by constructing the patient information model and utilizing the OMOP CDM standard terminology system; making full use the advantages of semantic technology in data interactivity and scalability, so that the system has better adaptability and scalability to heterogeneous data in different hospitals. At the same time, the clinical recommendations based on knowledge graph knowledge inference come from the clinical guidelines and physicians' experience in accordance with evidence-based medicine, and the inference process and recommendation reasons can be traced back by constructing inference individual, so that the inference process and recommendation reasons can be given while giving clinical recommendations, and the physicians' trust in decision support recommendations can be improved.

DESCRIPTION OF EMBODIMENTS

The present application will be further described in detail with reference to the attached drawings and specific embodiments.

Figure 1:
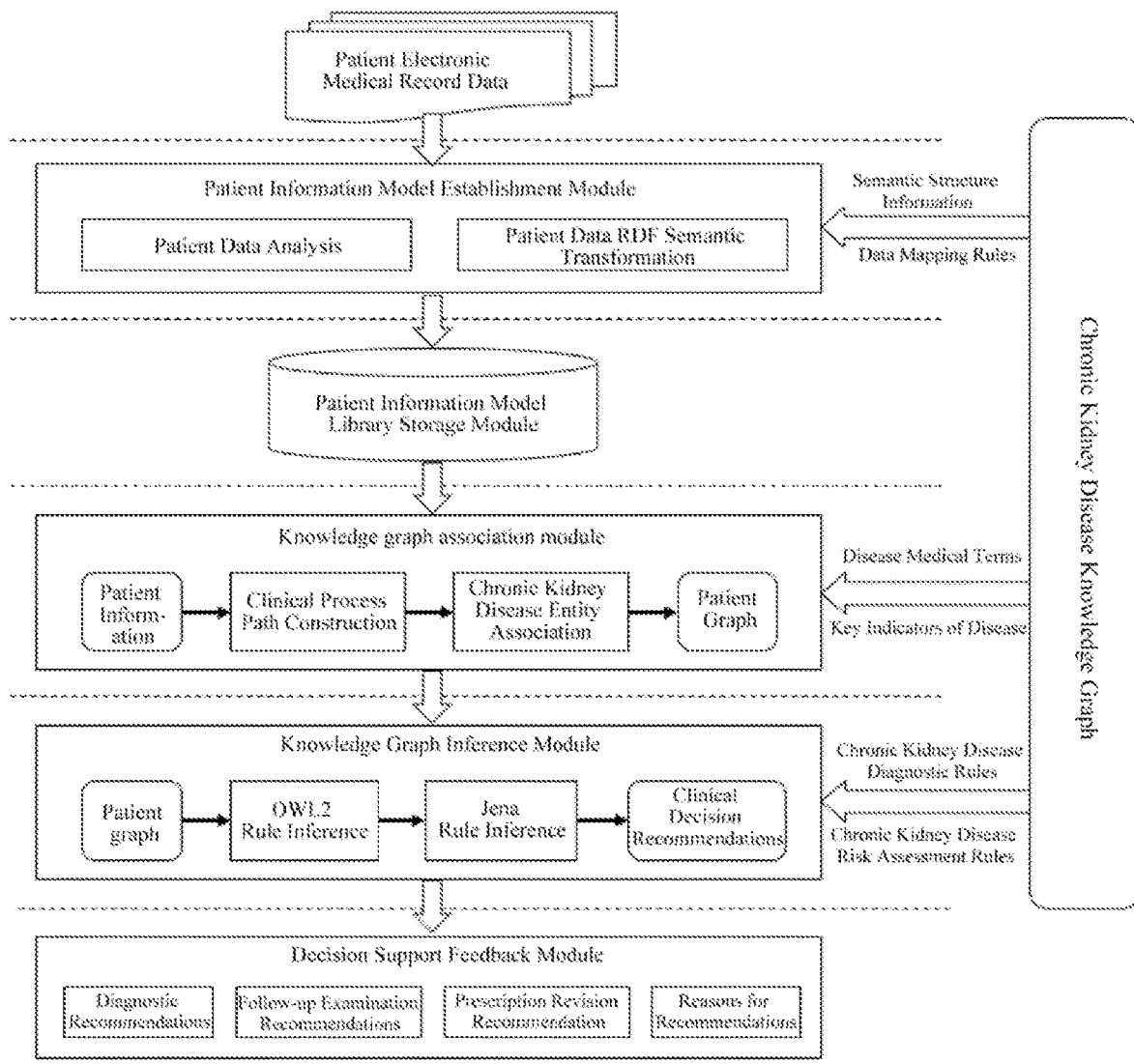
FIG. 1 is a structural frame diagram of the system of the present application.

As shown in FIG. 1, the cross-departmental decision support system for early diagnosis of a chronic kidney disease based on knowledge graph provided by the present application includes a patient information model building module, a patient information model library storage module, a knowledge graph association module, a knowledge graph inference module and a decision support feedback module.

Figure 2:
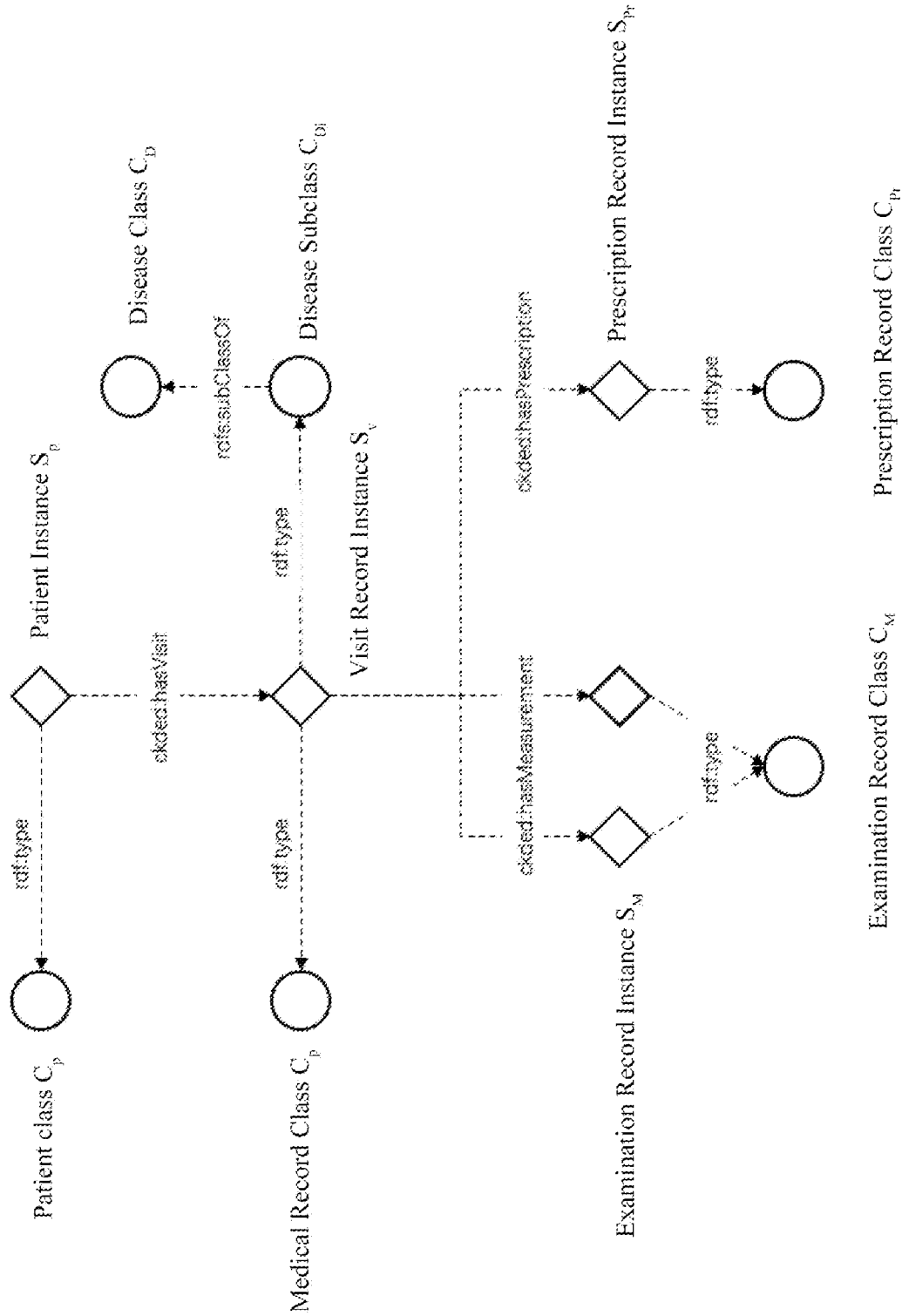
FIG. 2 is a patient information model structure.

The patient information model building module establishes a patient-centered knowledge sub-graph of patient electronic medical record data to form a patient information model based on the patient electronic medical record data according to the semantic structure of the chronic kidney disease knowledge graph (Chronic Kidney Disease Ontology, CKDO) and Observational Medical Outcomes Partnership Common Data Model (OMOP CDM) data structure; improves the applicability and portability of the system, and provides a standardized patient data model and structure for knowledge graph inference. The establishment of the model includes two processes: patient data analysis and RDF semantic transformation of patient data:

(1) patient data analysis process: according to the electronic medical record data of the patient, the patient data is divided into multiple hierarchical structures according to the chronic kidney disease knowledge graph and the standard terminology coding and structure of OMOP CDM; for each patient P, there are multiple medical records $V_i$(i=1 ... n), where $\{V_i|i=1 ... n\} \subset P$; wherein $V_i \cap V_j = \emptyset$, $(V_i, BV_j) \subset P$; each visit record $V_i$ spans a time period T, and for information such as any piece of diagnosis record D, examination record M, prescription record Pr and operation record Pc in the patient data, $\{D_h, M_j, Pr_k, Pc_m | h,j,k,m=1 ... n\} \subset V_i$ when a record time thereof is within the time period T; the concept coding, relationship type, value type and value information are extracted from subitems of D, M, Pr and Pc;

(2) a RDF semantic transformation process of the patient data: based on the analysis results of the patient data and the semantic structure of the chronic kidney disease knowledge graph, the patient electronic medical record data is constructed into a RDF (Resource Description Framework) triple relationship conforming to OWL (Web Ontology Language) language specification, and a data field is converted to standard OMOP CDM terminology coding through semantic mapping; for each patient P, visit record V, examination record M and prescription record Pr in the patient data, an ontology individual (owl:Individual) is constructed with a data ID thereof as a URI (Uniform Resource Identifier) to form a corresponding individual diagram $P_{ind}$=<P, rdf:type,owl:Individual>∈ $S_P$ (taking the patent individual as an example); for each patient individual $P_{ind}$, visit record individual $V_{ind}$, examination record individual $M_{ind}$ and prescription record individual $Pr_{ind}$, a corresponding ontology class relationship (owl:Class) is constructed to form a corresponding class diagram <$P_{ind}$,rdf:type,ckded:Patient>∈ $C_P$(taking the patent individual as an example); based on a hierarchical relationship intercepted in patient data analysis, association between the patient individual $P_{ind}$ and the visit record individual $V_{ind}$, association between the visit record individual $V_{ind}$ and the examination record individual $M_{ind}$, and association between the medical record individual $V_{ind}$ and the prescription record individual $Pr_{ind}$ are established through ontology object properties (owl:ObjectProperty) to form a patient data relationship diagram <$P_{ind}$,ckded:hasVisit,$V_{ind}$>∈ R and a medical record relationship diagram <$V_{ind}$,ckded:hasMeasurement,$M_{ind}$>; for each diagnostic record D and operation record Pc, a relationship between the related visit record individual $V_{ind}$ and a disease ontology class (e.g., <ckded: ChronicKidneyDisease,rdf:type,owl:Class>) and an operation record ontology class is established to form a corresponding class diagram <$V_{ind}$,rdf:type,ckded:ChronicKidneyDisease>∈ $C_D$ (taking the diagnosis class as an example); the patient data is constructed into RDF triple data according to the above rules, and the patient information model $G_P \supseteq (S_{P,V,M,Pr}, C_{P,V,M,Pr,D,Pc}, R)$ is formed. The patient information model in the form of RDF triples is shown in FIG. 2.

Figure 3:
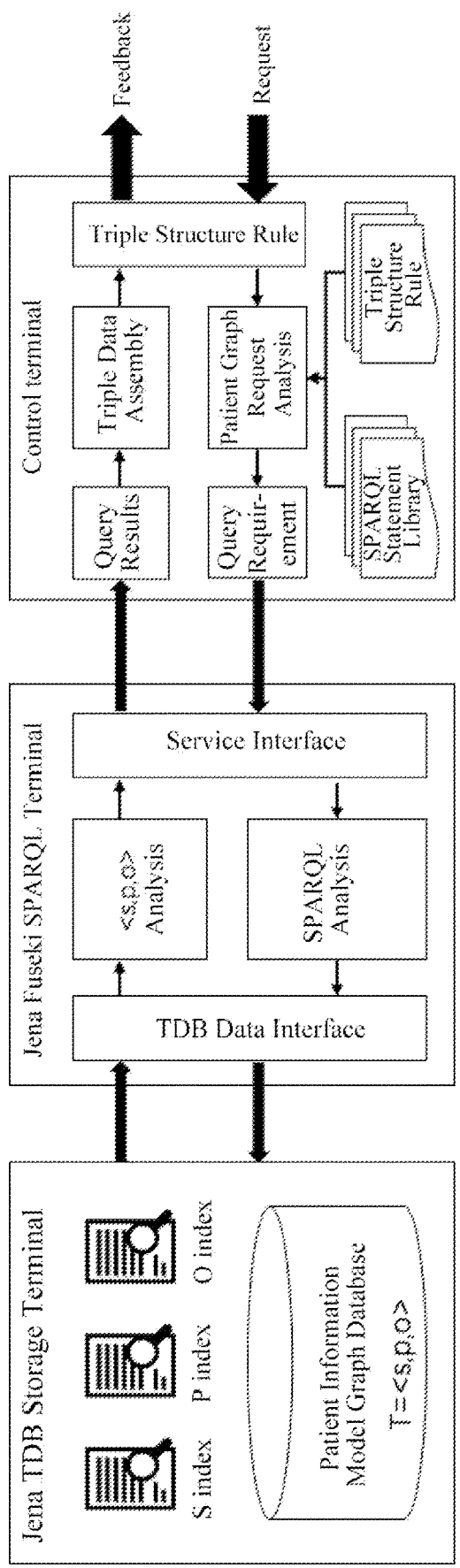
FIG. 3 is a structural diagram of a storage module of a patient information model library.
Figure 4:
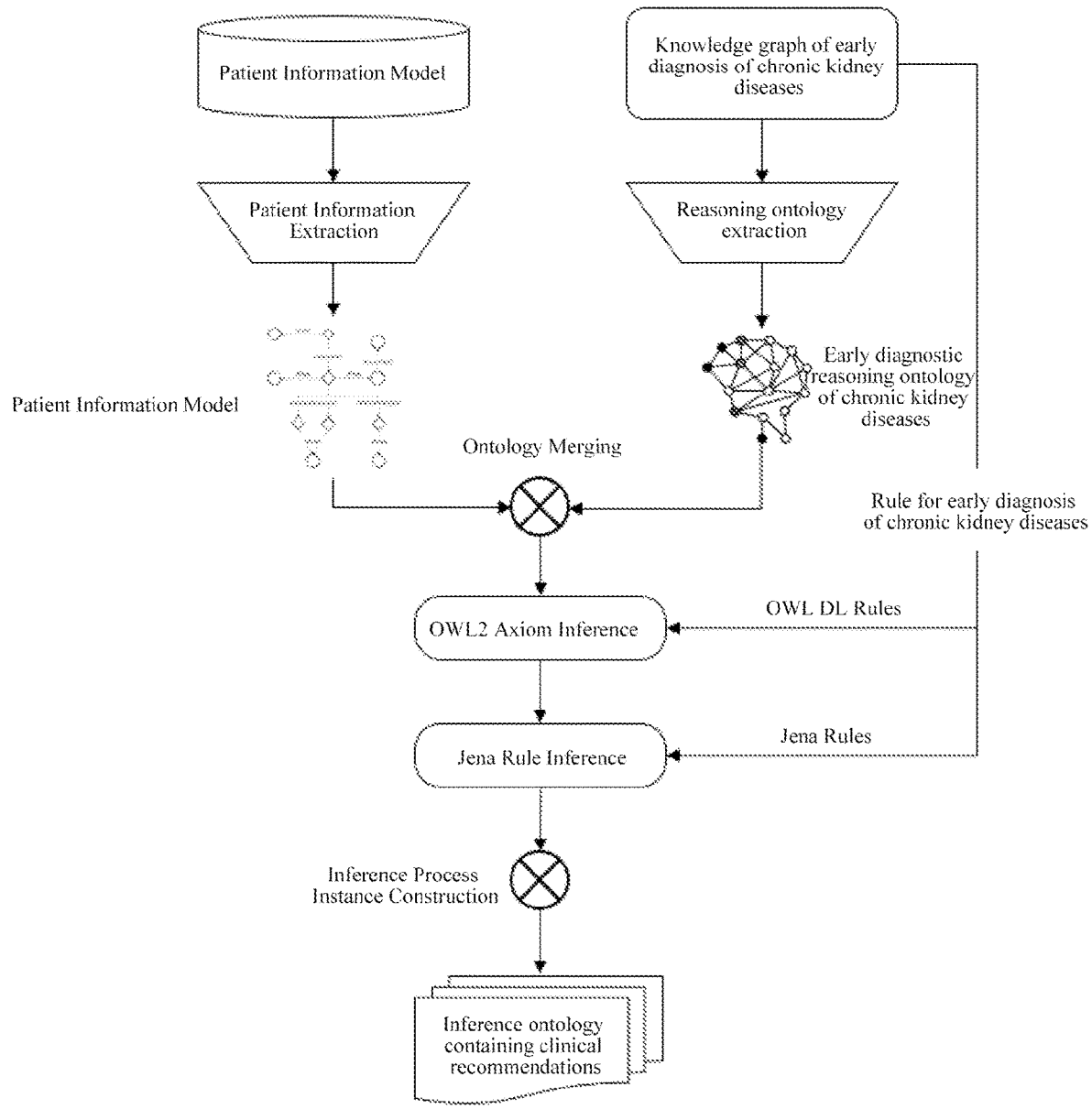
FIG. 4 is a structural diagram of the knowledge graph inference module.

The patient information model library storage module provides universal and efficient system support for saving and invoking the patient information model; stores the patient information model in a RDF triple form is stored by establishing a knowledge graph database, and provides the query and modification interface of the patient information model by a SPARQL endpoint; constructs a SPARQL query statement template according to the content and structure of patient data needed for early diagnosis of chronic kidney diseases, and provides a general method for retrieving the patient information model so as to support the decision support inference of the knowledge graph. The patient information model library storage module is divided into three parts: a Jena TDB memory terminal, a Jena Fuseki SPARQL endpoint and a control terminal, and the structure thereof is shown in FIG. 3.

The Jena TDB storage terminal is configured to build a knowledge graph database to store the patient information model in a form of RDF triples, wherein all patient information models converted into the RDF triples are recorded as N-Triple data files conforming to OWL language rules in a form of <s,p,o>; a RDF triple data set is stored and transformed by a Jena TDB Loader, and indices of a head element S, a relation element P and a tail element O of the RDF triple is established to improve the query speed.

The Jena Fuseki SPARQL endpoint is configured to build a RDF triple query and modification interface; the Jena Fuseki SPARQL endpoint invokes Jena TDB storage content, and invokes and modifies the patient information model through a W3C standard SPARQL query statement; the Jena Fuseki SPARQL endpoint is built in a Tomcat server, which monitors a SPARQL query request through a HTTP request and feeds back corresponding results.

The control terminal provides a target query and modification function for the patient information model; according to patient information model structure and knowledge graph inference requirements, a SPARQL query statement template is preset, and a request is sent to the Jena Fuseki SPARQL endpoint and the output result is formatted; for each patient $P_{ind}$, according to the clinical records in the patient information model, a result of a patient data relationship diagram is queried; based on the visit record individual $V_{ind}$ that has been fed back, a result of the medical record relationship diagram is queried; finally, the data property information is queried according to the examination record individual $M_{ind}$ and the operation record individual $P_{rIND}$; the control terminal sets SPARQL query statements based on the above principles, and establishes a result graph for feedback.

The knowledge graph association module enriches semantic information of the patient information model, and associates scattered clinical record RDF triples in the patient information model according to a real world clinical diagnosis and treatment process sequence; associates individuals of medical examinations, clinical complaints and prescription records with clinical findings, clinical diagnoses and disease risks based on a medical concept relationship in the chronic kidney disease knowledge graph. The knowledge graph association module is implemented as follows:

the chronic kidney disease knowledge graph is defined as G=(V,A), and the patient information model is defined as G'=(V',A'), where G and G' are two directed graphs, V and V' are nodes in the graph, and A and A' are directed edges in the graph; the knowledge graph association module completes V and A' of the graph G' based on the relationship in the graph G; for any v∈V and any v'∈V', node similarities sim(v,v') and sim'(v',v) are calculated, and the similarity through cos similarity; at the same time, similarity matching is carried out according to a standard concept coding hierarchy relationship between nodes v and v'; a similar node pair is recorded as $b=\min|sim(v_i,v_j')-sim'(v_j',v_i)|$, a set thereof is b∈B, and the node pairs $v_i$ and $v_j$ contained in B are candidate associated node pairs; for the candidate association node pairs, the semantic association similarity of the nodes is calculated, and the triple relationship is supplemented to the patient information model according to the similar association, so as to improve the information; a triple $(v_i,a,v_j)\in V\times A\times V$ is established for the node v and directed edge A, where $(v_i,a,v_j)$ conforms to the graph relationship of G=(V,A); the calculation of semantic association is recorded as rel(v,a)={x|v,x∈V∧(v,a,x)∈A}; for each patient information model node $v_i'$, $sim(v,v_i)$ of the corresponding knowledge graph node v is calculated, where $(v,v_i)\in V$ and $v_i\ne v$; all node pairs v and vi whose sim(v,vi) is greater than the threshold k are taken, and if v and vi conform to rel(v,a) relationship, a $<v_i',a,v_i>$ triple association to the node $v_i'$ of the patient information model is added, thereby realizing semantic information completion of the patient information model based on the chronic kidney disease knowledge graph.

The knowledge graph inference module reasons diagnosis deficiency, disease risk diagnosis deficiency, disease follow-up requirement deficiency and prescription adjustment for the chronic kidney disease of a patient based on the RDF triple relationship of clinical records in the patient information model and clinical recommendation inference rules in the chronic kidney disease knowledge graph, and provides corresponding clinical diagnosis recommendations, risk recommendations, follow-up requirement recommendations and prescription adjustment recommendations based on inference results. The knowledge graph inference module is implemented as follows:

firstly, the patient information model is invoked to analyze the RDF triple relationship therein; at the same time, an inference ontology copy $O_n$ is established from the chronic kidney disease knowledge graph, and according to each individual S and an ontology class C to which the individual S belongs in the patient information model, the individual is constructed into an ontology class C' corresponding to the inference ontology copy $O_n$; each individual S and a relation graph R thereof in the patient information model are extracted to obtain a<$s_i,r,s_j$>triple, where $(S_i,S_j)\in S, r\in R$, which is reconstructed in the inference ontology copy on; each individual S and a data property relationship $R_S$ and an attribute Value $V_a$ thereof in the patient information model are extracted to obtain a<$s,r_S,v_a$>triple, where $s\in S, r_S\in R_S$, $v_a\in V_a$, which is reconstructed in the inference ontology copy $O_n$, in the above steps, the inference ontology copy on of chronic kidney disease knowledge graph containing patient information is constructed to provide basic elements for semantic inference;

then, based on OWL2 DL rules in the chronic kidney disease knowledge graph, by using the Fact++inference engine, according to the patient information in the inference ontology copy $O_n$, the patient individual $S_P$, the visit record individual SV, the examination record individual $S_M$ and the prescription record individual $S_{Pr}$ are subjected to ontology class affiliation completion and missing object property establishment; according to OWL2 DL rules in the chronic kidney disease knowledge graph, the data in the patient information model, such as examination record individuals of abnormal glomerular filtration rate, prescription record individuals containing drugs that may damage renal function, and visit record individuals containing chief complaints of chronic kidney disease symptoms, are associated with the chronic kidney disease risk ontology class; object property association is established for the visit record individual $S_{v'}$ including abnormal examination record individual $S_{M'}$ and prescription record individual $S_{PR'}$, and abnormal records in the visit records are marked;

according to Jean Rules established in the clinical guidelines for chronic kidney diseases, by using Jena inference engine, the association between a patient individual $S_P$ and a visit record individual $S_v$ and a clinical recommendation individual $S_{re}$ such as disease diagnosis, risk factors, follow-up plans and drug adjustment plans in the chronic kidney disease knowledge graph is established through semantic inference based on the individual data and the individual relationship in the patient information model, thus forming clinical recommendation contents based on the patient's condition; the Jean Rules established in the clinical guidelines for chronic kidney diseases are divided into diagnosis rules, risk classification rules, follow-up screening rules and prescription adjustment rules for chronic kidney diseases; the above rules are based on a Jena Rules standard language, and are established according to the paradigm of [rule name: (triple 1) (triple 2) . . . operator 1 (operand) operator 2 (operand) . . . →(triple N) (triple N+1) . . .]; the medical source for the rules is clinical guidelines for chronic kidney diseases such as "KDIGO 2012 Clinical Practice Guideline", "Practical Approach to Detection and Management of Chronic Kidney Disease for the Primary Care Clinician" and "Detection and Evaluation of Chronic Kidney Disease"; according to the specifications of diagnosis, risk grading, follow-up screening and prescription adjustment for chronic kidney diseases the in clinical guidelines, RDF triples containing medical examination results, chief complaint symptoms, disease history, prescription and other information of the patient are established on the left side of the arrow as conditions, a numerical value of that examination result is judged by operators and operands, and RDF triples of disease diagnosis, risk classification, follow-up screening and prescription adjustment are established on the right side of the arrow when the conditions on the left side of the arrow are met; the Jena inference engine implements inference according to the RDF triple information corresponding to the patient individual $S_P$ in the patient information model based on the requirements on the left side of the arrow, and adds a decision support recommendation RDF triple on the right side of the arrow to the patient individual $S_P$ that meets the rules;

according to the inference rules triggered by a Fact++ inference engine and a Jena inference engine, the inference individual $S_R$ is established, and the inference individual $S_R$ is configured to record the clinical knowledge in the clinical guidelines involved in inference; attributes of a relation between the inference individual $S_R$ and the visit record individual $S_v$, the examination record individual $S_M$ and the prescription record $S_{Pr}$ involved in the inference rules are established, so as to establish inference result association for the clinical recommendations and provide a recommendation reason inference process record.

In addition to using Fact++ and Jena inference engines for rule inference, the inference engines can also be replaced by a HermiT inference engine, an ELK inference engine and a Pellet inference engine, etc. The replacement of inference engines only changes the tools used in the process of realizing semantic inference.

The decision support feedback module feeds back the clinical diagnosis recommendations, risk recommendations, follow-up requirement recommendations and prescription adjustment recommendations provided by the knowledge graph inference module, and a clinical recommendation report containing inference process of above recommendations to a physician. The decision support feedback module is specifically implemented as follows:

the class, object property and data property content of the patient individual $S_P$ in a regular inference ontology $O_n$ are queried through a preset SPARQL query statement, the obtained RDF graph results are analyzed, and the relevant information (concept coding, concept name, numerical value, text information, etc.) of tail nodes in the RDF triple are extracted, so as to obtain the newly established individual $S_{re}$ of diagnosis, risk, follow-up recommendations and prescription adjustment recommendations for the chronic kidney disease; the diagnosis, the risk, the follow-up recommendations and the prescription adjustment recommendations for the chronic kidney diseases that are newly established by the inference module are obtained from $S_{re}$, and a clinical recommendation report containing inference process is formed by combining an inference path relationship recorded in the inference individual $S_R$ corresponding to the patient individual $S_P$ and the recommendation individual $S_{RE}$ for feedback to physicians.

According to the present application, based on the semantic structure of the chronic kidney disease early diagnosis knowledge graph and the OMOP CDM data model, the patient electronic medical record data is converted into a semantic patient information model, and the concept coding and semantic structure are unified, thereby realizing semantic standardization of heterogeneous medical data in different hospitals and improving system adaptability and expansibility. The patient information model is subjected to knowledge association based on ontology matching, independent and scattered patient data is integrated with clinical knowledge of chronic kidney diseases in the knowledge graph, the patient information model is enriched, clinical process association is introduced, and knowledge and data basis for semantic inference is provided. By using a Fact++ inference engine and a Jena inference engine, based on the clinical recommendation rules of early diagnosis of chronic kidney diseases in the knowledge graph, semantic inference is carried out from two aspects of OWL2 axiom and Jean complex rules, and the diagnosis results, risk grade, follow-up requirements and prescription adjustment requirements of patients with chronic kidney disease are analyzed. The inference process builds an individual of an inference process, records inference path and reasons for recommendations, gives reasons for recommendations and inference process while providing clinical recommendations, and thus improves physicians' trust. According to the present application, effective support is provided for early diagnosis of chronic kidney diseases by utilizing the characteristics of knowledge explicitation, strong data interactivity and strong expansibility of the knowledge graph.

The above is only an embodiment of the present application, and is not intended to limit the scope of protection of the present application. Any modification, equivalent substitution, improvement and the like made without creative labor within the spirit and principle of the present application are included in the protection scope of the present application.

What is claimed is:

1. A cross-departmental decision support system for early diagnosis of a chronic kidney disease based on knowledge graph, which is configured to provide clinical decision support of chronic kidney disease for patients in non-nephrology department, including diagnosis, risk level, follow-up requirements and prescription adjustment, comprising:

at least one processor, and a memory configured to store instructions executable by the at least one processor;

wherein the instructions cause the at least one processor to:

acquire electronic medical record data and construct a semantic structure of a chronic kidney disease knowledge graph and an OMOP CDM data structure;

build a patient information model based on electronic medical record data and according to the semantic structure of the chronic kidney disease knowledge graph and the OMOP CDM data structure, wherein the patient information model functions as a subset of knowledge graph, and consists of patient-centered medical information from the electronic medical record;

provide support for storage and invoking the patient information model, stores the patient information model by inserting a RDF triple into knowledge graph database, provide a query and modification interface of the patient information model by establishing a SPARQL endpoint for executing query, update command of the patient information model in a knowledge graph database, and construct a SPARQL query template for the query and modification interface according to a structure of the patient information model and patient data needed for early diagnosis of the chronic kidney disease, wherein the SPARQL query template serves as general method for retrieving the patient information model, so as to support a knowledge graph inference of a decision support;

enrich semantic information of the patient information model, and associates scattered clinical record RDF triples in the patient information model according to a real world clinical diagnosis and treatment process sequence, and associate individuals of examinations, clinical complaints and prescription records with clinical findings, clinical diagnoses and disease risks based on a medical concept relationship in the chronic kidney disease knowledge graph;

reason diagnosis deficiency, disease risk diagnosis deficiency, disease follow-up requirement deficiency and prescription adjustment for the chronic kidney disease of a patient based on the RDF triple relationship of clinical records in the patient information model and clinical recommendation inference rules in the chronic kidney disease knowledge graph, and provide corresponding clinical diagnosis recommendations, risk recommendations, follow-up requirement recommendations and prescription adjustment recommendations based on inference results; and generate decision support data based on the inference results of the clinical diagnosis recommendations, the risk recommendations, the follow-up requirement recommendations and the prescription adjustment recommendations, form a clinical recommendation report according to the decision support data, and feed back the clinical diagnosis recommendations, the risk recommendations, the follow-up requirement recommendations, the prescription adjustment recommendations, and the clinical recommendation report containing inference process of the clinical diagnosis recommendations, the risk recommendations, the follow-up requirement recommendations and the prescription adjustment recommendations to a physician;

wherein said building the patient information model comprises two processes which are patient data analysis and patient data RDF semantic transformation:

(1) a patient data analysis process: according to the electronic medical record data of the patient, the patient data is divided into multiple hierarchical structures according to the chronic kidney disease knowledge graph and the standard terminology coding and structure of OMOP CDM; for each patient P, there are multiple visit records $V_i(i=1 \ldots n)$, where $\{V_i | i=1 \ldots n\} \subset P$; wherein $v_i \cap V_j = \emptyset$, $(V_i, v_j) \subset P$; each visit record $V_i$ spans a time period T, and for information such as any piece of diagnosis record D, examination record M, prescription record Pr and operation record Pc in the patient data, $\{D_h, M_j, Pr_k, Pc_m | h,j,k,m=1 \ldots n\} \subset V_i$ when a record time thereof is within the time period T; the concept coding, relationship type, value type and value information are extracted from subitems of D, M, Pr and Pc; and (2) a RDF semantic transformation process of the patient data: based on the analysis results of the patient data and the semantic structure of the chronic kidney disease knowledge graph, the patient electronic medical record data is constructed into a RDF triple relationship conforming to OWL language specification, and a data field is converted to standard OMOP CDM terminology coding through semantic mapping; for each patient P, visit record V, examination record M and prescription record Pr in the patient data, an ontology individual is constructed with a data ID thereof as a URI to form a corresponding individual diagram; for each patient individual $P_{ind}$, visit record individual $V_{ind}$, examination record individual $M_{ind}$ and prescription record individual $Pr_{ind}$, a corresponding ontology class relationship is constructed to form a corresponding class diagram; based on a hierarchical relationship intercepted in patient data analysis, association between the patient individual $P_{ind}$ and the visit record individual $V_{ind}$, association between the visit record individual $V_{ind}$ and the examination record individual $M_{ind}$, and association between the visit record individual $V_{ind}$ and the prescription record individual $Pr_{ind}$ are established through ontology object properties to form a patient data relationship diagram and a visit record relationship diagram; for each diagnostic record D and operation record Pc, a relationship between the related visit record individual $V_{ind}$ and a disease ontology class and an operation record ontology class is established to form a corresponding class diagram; the patient data is constructed into RDF triple data according to the above rules, and the patient information model is formed.

2. The cross-departmental decision support system for early diagnosis of a chronic kidney disease based on knowledge graph according to claim 1, wherein a patient information model is stored in a patient information model database, and wherein the patient information model database is divided into three parts: a Jena TDB storage terminal, a Jena Fuseki SPARQL endpoint and a control terminal;

the Jena TDB storage terminal is configured to build a knowledge graph database to store the patient information model in a form of RDF triples, wherein all patient information models converted into the RDF triples are recorded as N-Triple data files conforming to OWL language rules in a form of <s,p,o >; a RDF triple data set is stored and transformed by a Jena TDB Loader, and indices of a head element S, a relation element P and a tail element O of the RDF triple is established to improve the query speed;

the Jena Fuseki SPARQL endpoint is configured to build a RDF triple query and modification interface; the Jena Fuseki SPARQL endpoint invokes Jena TDB storage content, and invokes and modifies the patient information model through a W3C standard SPARQL query statement; the Jena Fuseki SPARQL endpoint is built in a Tomcat server, which monitors a SPARQL query request through a HTTP request and feeds back corresponding results; and the control terminal provides a target query and modification function for the patient information model; according to patient information model structure and knowledge graph inference requirements, a SPARQL query statement template is preset, and a request is sent to the Jena Fuseki SPARQL endpoint and the output result is formatted; for each patient $P_{ind}$, according to the clinical records in the patient information model, a result of a patient data relationship diagram is queried; based on the visit record individual $V_{ind}$ that has been fed back, a result of the medical record relationship diagram is queried; finally, the data property information is queried according to the examination record individual Mind and the operation record individual Prind; the control terminal sets SPARQL query statements based on above principles, and establishes a result graph for feedback.

3. The cross-departmental decision support system for early diagnosis of a chronic kidney disease based on knowledge graph according to claim 1, wherein the nodes and relations in the knowledge graph is associated as follows:

the chronic kidney disease knowledge graph is defined as G=(V,A), and the patient information model is defined as G'=(V',A'), where G and G' are two directed graphs, V and V' are nodes in the graph, and A and A' are directed edges in the graph; the knowledge graph association module completes V and A' of graph G' based on the relationship in graph G; for any $v \in V$ and any $v' \in V'$, node similarities $sim(v,v')$ and $sim'(v',v)$ are calculated through cos similarity; at the same time, similarity matching is carried out according to a standard concept coding hierarchy relationship between nodes v and v'; a similar node pair is recorded as $b=min|sim(v_i,v_j')-sim'(v_j',v_i)|$, a set thereof is $b \in B$, and the node pairs $v_1$ and $v_j$ contained in B are candidate associated node pairs; for the candidate association node pairs, the semantic association similarity of the nodes is calculated, and the triple relationship is supplemented to the patient information model according to the similar association, so as to improve the information; a triple $(v_i,a,v_j) \in V \times A \times V$ is established for node v and directed edge A, where $(v_i,a,v_j)$ conforms to graph relationship of $G=(V,A)$; the calculation of semantic association is recorded as $rel(v,a)=\{x|v,x \in V \wedge (v,a,x) \in A\}$; for each patient information model node $v_i'$, $sim(v,v_i)$ of the corresponding knowledge graph node v is calculated, where $(v,v_i) \in V$ and $v_i \neq v$; all node pairs v and vi whose $sim(v,vi)$ is greater than a threshold k are taken, and if v and vi conform to $rel(v,a)$ relationship, a $<v_i',a,v_i>$triple association to the node $v_i'$ of the patient information model is added, thereby realizing semantic information completion of the patient information model based on the chronic kidney disease knowledge graph.

4. The cross-departmental decision support system for early diagnosis of a chronic kidney disease based on knowledge graph according to claim 1, wherein knowledge graph is inferenced as follows:

firstly, the patient information model is invoked to analyze the RDF triple relationship therein; at the same time, an inference ontology copy $O_n$ is established from the chronic kidney disease knowledge graph, and according to each individual S and an ontology class C to which the individual S belongs in the patient information model, the individual is constructed into an ontology class C' corresponding to the inference ontology copy $O_n$; each individual S and a relation graph R thereof in the patient information model are extracted to obtain a$<s_i,r,s_j>$triple, where $(s_i,s_j) \in S, r \in R$, which is reconstructed in the inference ontology copy on; each individual S and a data property relationship $R_S$ and an attribute Value $V_a$ thereof in the patient information model are extracted to obtain a$<s,r_S,v_a>$triple, where $s \in S, r_S \in R_S, v_a \in V_a$, which is reconstructed in the inference ontology copy $O_n$; in the above steps, the inference ontology copy $O_n$ of chronic kidney disease knowledge graph containing patient information is constructed to provide basic elements for semantic inference;

then, based on OWL2 DL rules in the chronic kidney disease knowledge graph, by using the Fact++inference engine, according to the patient information in the inference ontology copy $O_n$, the patient individual $S_P$, the visit record individual SV, the examination record individual $S_M$ and the prescription record individual $S_{pr}$ are subjected to ontology class affiliation completion and missing object property establishment; according to OWL2 DL rules in the chronic kidney disease knowledge graph, the data in the patient information model, such as examination record individuals of abnormal glomerular filtration rate, prescription record individuals containing drugs that may damage renal function, and visit record individuals containing chief complaints of chronic kidney disease symptoms, are associated with the chronic kidney disease risk ontology class; object property association is established for the visit record individual $S_V$, including abnormal examination record individual $S_M$ and prescription record individual $S_{pr}$, and abnormal records in the visit records are marked;

according to Jean Rules established in the clinical guidelines for chronic kidney diseases, by using Jena inference engine, the association between a patient individual $S_P$ and a visit record individual $S_V$ and a clinical recommendation individual $S_{re}$ such as disease diagnosis, risk factors, follow-up plans and drug adjustment plans in the chronic kidney disease knowledge graph is established through semantic inference based on the individual data and the individual relationship in the patient information model, thus forming clinical recommendation contents based on the patient's condition; the Jean Rules established in the clinical guidelines for chronic kidney diseases are divided into diagnosis rules, risk classification rules, follow-up screening rules and prescription adjustment rules for chronic kidney diseases; above rules are compiled based on a Jena Rules standard language, and are established according to the paradigm of [rule name: (triple 1) (triple 2) . . . operator 1 (operand) operator 2 (operand) . . . →(triple N) (triple N+1) . . .]; according to the specifications of diagnosis, risk grading, follow-up screening and prescription adjustment for chronic kidney diseases the in clinical guidelines, RDF triples containing medical examination results, chief complaint symptoms, disease history, prescription and other information of the patient are established on the left side of the arrow as conditions, a numerical value of that examination result is judged by operators and operands, and RDF triples of disease diagnosis, risk classification, follow-up screening and prescription adjustment are established on the right side of the arrow when the conditions on the left side of the arrow are met; the Jena inference engine implements inference according to the RDF triple information corresponding to the patient individual Sp in the patient information model based on the requirements on the left side of the arrow, and adds a decision support recommendation RDF triple on the right side of the arrow to the patient individual $S_P$ that meets the rules; and according to the inference rules triggered by a Fact++ inference engine and a Jena inference engine, the inference individual $S_R$ is established, and the inference individual $S_R$ is configured to record the clinical knowledge in the clinical guidelines involved in inference; attributes of a relation between the inference individual $S_R$ and the visit record individual $S_V$, the examination record individual $S_M$ and the prescription record $S_{pr}$ involved in the inference rules are established, so as to establish inference result association for the clinical recommendations and provide a recommendation reason inference process record.

5. The cross-departmental decision support system for early diagnosis of a chronic kidney disease based on knowledge graph according to claim 1, wherein the decision support is fedback as follows:

the class, object property and data property content of the patient individual $S_P$ in a regular inference ontology $O_n$ are queried through a preset SPARQL query statement, the obtained RDF graph results are analyzed, and the relevant information (concept coding, concept name, numerical value, text information, etc.) of tail nodes in the RDF triple are extracted, so as to obtain a newly established individual $S_{re}$ of diagnosis, risk, follow-up recommendations and prescription adjustment recommendations for the chronic kidney disease; the diagnosis, the risk, the follow-up recommendations and the prescription adjustment recommendations for the chronic kidney diseases that are newly established by the inference module are obtained from $S_{re}$, and meanwhile a clinical recommendation report containing inference process is formed by combining an inference path relationship recorded in the inference individual $S_R$ corresponding to the patient individual Sp and the recommendation individual $S_{RE}$ for feedback to physicians.

\* \* \* \* \*